US010154809B2

(12) United States Patent
Vereshchetin et al.

(10) Patent No.: US 10,154,809 B2
(45) Date of Patent: Dec. 18, 2018

(54) TEST STRIP DEVICE AND RELATED METHODS THEREOF

(71) Applicant: University of Virginia Patent Foundation, Charlottesville, VA (US)

(72) Inventors: Pavel Vereshchetin, Charlottesville, VA (US); Molly McElwee-Malloy, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/192,468

(22) Filed: Jun. 24, 2016

(65) Prior Publication Data

US 2016/0374604 A1 Dec. 29, 2016

Related U.S. Application Data

(60) Provisional application No. 62/183,941, filed on Jun. 24, 2015.

(51) Int. Cl.

*A61B 5/1486* (2006.01)
*A61B 5/15* (2006.01)
*G01N 27/327* (2006.01)
*A61B 5/151* (2006.01)

(Continued)

(52) U.S. Cl.

CPC ...... *A61B 5/150717* (2013.01); *A61B 5/1486* (2013.01); *A61B 5/14532* (2013.01); *A61B 5/150022* (2013.01); *A61B 5/15105* (2013.01); *A61B 5/150358* (2013.01); *A61B 5/150419* (2013.01); *A61B 5/150572* (2013.01); *A61B 5/150664* (2013.01); *G01N 27/3272* (2013.01); *G01N 33/4875* (2013.01);

(Continued)

(58) Field of Classification Search

CPC ........................................................ A61B 5/14

See application file for complete search history.

(56) References Cited

U.S. PATENT DOCUMENTS 4,858,607 A 8/1989 Jordan
5,707,384 A 1/1998 Kim
5,868,772 A 2/1999 Levaughn (Continued)

FOREIGN PATENT DOCUMENTS

EP 0874984 11/2001
WO WO 02/100253 12/2002

OTHER PUBLICATIONS

Wang, "Electrochemical glucose biosensors," Chem Rev 108:814-825, 2008.*

*Primary Examiner* — Rosanne Kosson
(74) *Attorney, Agent, or Firm* — Robert J. Decker

(57) ABSTRACT

An electrochemical biosensor test strip device and compatible meter or processor for determining the amount of an analyte in a liquid sample received from a subject. The device may include: a substrate having a liquid sampling end and an electrical contact end; a circuit disposed in communication with the substrate; a reaction area formed at the liquid sampling end of the substrate; and a lancet having a pointed end and an opposite end, whereby the opposite end of the lancet is disposed in communication with the substrate and located at the reaction area. The device may also include an interface area that may be separate or integrated as part the reaction area (or the reaction area may be integrated with interaction area).

35 Claims, 10 Drawing Sheets

(51) Int. Cl.
*A61B 5/145* (2006.01)
*G01N 33/487* (2006.01)

(52) U.S. Cl.
CPC ... *A61B 5/14546* (2013.01); *A61B 2562/0295* (2013.01); *G01N 27/3273* (2013.01)

(56) References Cited

U.S. PATENT DOCUMENTS

| | | | |
|---|---|---|---|
| 5,951,492 | A | 9/1999 | Douglas |
| 5,954,738 | A | 9/1999 | Levaughn |
| 6,099,484 | A | 8/2000 | Douglas |
| 6,264,619 | B1 | 7/2001 | Ferguson |
| 6,468,287 | B1 | 10/2002 | Baugh |
| 6,706,159 | B2 | 3/2004 | Moerman |
| 6,719,771 | B1 | 4/2004 | Crossman |
| 7,112,265 | B1 | 9/2006 | McAleer |
| 7,175,643 | B2 | 2/2007 | Shi |
| 7,343,188 | B2 | 3/2008 | Sohrab |
| 7,374,546 | B2 | 5/2008 | Roe |
| 7,378,007 | B2 | 5/2008 | Moerman |
| 7,875,461 | B2 | 1/2011 | Docherty |
| 7,972,349 | B2 | 7/2011 | Crossman |
| 8,025,628 | B2 | 9/2011 | Wong |
| 8,357,107 | B2 | 1/2013 | Draudt |
| 8,636,672 | B2 | 1/2014 | Neel |
| 2003/0088191 | A1 | 5/2003 | Freeman |
| 2004/0006285 | A1 | 1/2004 | Douglas |
| 2004/0182703 | A1 | 9/2004 | Bell |
| 2005/0240119 | A1 | 10/2005 | Draudt |
| 2006/0129172 | A1 | 6/2006 | Crossman |
| 2006/0229532 | A1 | 10/2006 | Wong |
| 2007/0193882 | A1 | 8/2007 | Dai |
| 2008/0021291 | A1 | 1/2008 | Zocchi |
| 2008/0208078 | A1 | 8/2008 | Neel |
| 2008/0243032 | A1* | 10/2008 | Hindelang ......... A61B 5/14532 600/583 |
| 2009/0057146 | A1 | 3/2009 | Teodorcyzk |
| 2009/0299224 | A1 | 12/2009 | Yoo |
| 2009/0302872 | A1 | 12/2009 | Haggett |
| 2010/0081968 | A1 | 4/2010 | Neel |
| 2010/0198107 | A1 | 8/2010 | Groll |
| 2011/0284393 | A1 | 11/2011 | Macfie |

* cited by examiner

TEST STRIP DEVICE AND RELATED METHODS THEREOF

RELATED APPLICATIONS

The present application claims priority of priority under 35 U.S.C. § 119 (e) from U.S. Provisional Application Ser. No. 62/183,941, filed Jun. 24, 2015, entitled "Lancing Strip Device and Related Method," the disclosure of which is hereby incorporated by reference herein in its entirety.

FIELD OF THE INVENTION

The present invention relates generally to the field of diagnostic testing and, more particularly, to diagnostic testing devices and systems using electrochemical biosensors.

BACKGROUND

The traditional glucometer and related supplies consists of a meter, test strips, a lancing device and lancets. The ability to port this set of tools can vary depending upon the individual and with less portability comes less compliance. In particular, insulin use for Type 2 Diabetes carries the importance of checking blood glucose several times a day, at meal time and between meals to see if current therapies are effective. The adherence to therapy is detrimentally affected due to the associated challenges of the patient to both carry and discretely check blood glucose. There is a long felt need for providing a more compact solution that allows for ease of checking on the go and increased privacy. There is a long felt need of diminishing the burden on the patient so as to increase patient compliance to checking blood glucose.

The present inventors note at least two problems, among others, associated with a traditional glucose testing strip. For example, the present inventors note that traditional glucose testing strips requires the use of a blood-sampling device loaded with a lancet. The present inventors note that ideally, the lancets should be used only once. Currently, there is an additional burden in diabetes management to change the lancet. Currently, lancets are expensive. Moreover, the present inventors note that the current blood-sampling devices are designed in a way that poses the risk of accidental involuntary pricking when changing the lancet. As such, the present inventors note that these factors discourage the patients from switching the lancet which increases the risks of infection. The present inventors note that current lancets cannot be disposed into regular trash due to blood on it that can have bioactive elements in it for some time after disposal. Thus it requires special care when discarding.

SUMMARY OF EXEMPLARY EMBODIMENTS OF THE INVENTION

An aspect of an embodiment of the present invention provides, among other things, a disposable blood glucose strip and related method that does not require a blood sampling device and does not require a standalone lancet. An aspect of an embodiment of the present invention provides, among other things, a strip device that includes a small needle (such as a lancet or other knife or sharp surgical instrument) as a part of an integrated design. Thus the strip device itself serves as the lancet. After the use, an embodiment of the strip device can be disposed as a glucose sample strip—whereby the blood is securely contained inside the strip device and does not pose a biohazard. An aspect of an embodiment of the strip device may include an end that includes a cover, such as a foil cover, that would need to be removed for patient/caregiver use. Thus, the cover is configured to protect individuals (e.g., users, subjects, practitioners, caregivers, etc.) from accidental sticks and ensuring the sterility of the needle. An aspect of an embodiment may be configured to include a raised bed (or the like) that may be may be made of a rubber like material (or other selected material as desired or required) with raised points or protrusions to "confuse" the skin and enable an easier fingerstickor the like. In one aspect, the subject being in contact with the raised bed of protrusions (e.g., sensory blunt contact points) provides sensory signal distractions to the subject.

The present inventors note that an aspect of an embodiment of the strip device may be referred to as a prototype or portion of the prototype referred to as the "Lanstrip".

In a particular application, for example, insulin use for Type 2 Diabetes carries the importance of checking blood glucose several times a day, at meal time and between meals to see if current therapies are effective. The ability of the patient to both carry and discretely check blood glucose affects adherence to therapy. Accordingly, an aspect of an embodiment of the present invention provides, other things, providing a more compact solution allows for ease of checking on the go and increased privacy. By diminishing the burden on the patient, the present inventors forecast increased compliance to checking blood glucose or other applicable monitoring of analytes or the like.

An aspect of various embodiments of the present invention provide a number of novel and nonobvious features, elements and characteristics, such as but not limited thereto, as discussed below. An aspect of an embodiment of the present invention device provides the inclusion of the needle (lancet) in the strip's design that, therefore, renders the blood sampling device and separate lancets unnecessary. An aspect of an embodiment of the present invention device may include an absorbing sponge, foam, or the like that catches and contains the blood. An aspect of an embodiment of the present invention device provides a bendable and sealable design of the strip that further ensures that the blood cannot escape after the strip is used.

An aspect of various embodiments of the present invention device may provide a number of advantages, such as but not limited thereto, the following: using the device does not require blood-sampling device (lancet device); using the device does not require separate lancets; using the device allows for the sampling to occur at the reaction area, using the device does not require active firing or activation of a lancet, and using the device does not require special recycling and can be disposed of into regular trash.

An aspect of various embodiments of the present invention strip device may be utilized for a number of products and services, such as but not limited thereto, blood glucose testing by type I and type 2 diabetics or for other use (such as testing of other analytes or materials) by anybody (patient, subject, animal) who needs to produce a small capillary blood sample or the like.

In diabetic field and other analytical fields, an aspect of an embodiment of the present invention provides the potential to become an alternative industry standard for testing blood glucose or other analytes or materials.

An aspect of an embodiment of the present invention provides, among other things, an electrochemical biosensor test strip device for determining the amount of an analyte in a liquid sample received from a subject. The device may comprise: a substrate having a liquid sampling end and an electrical contact end; a circuit disposed in communication with the substrate; a reaction area formed at the liquid sampling end of the substrate; and a lancet having a pointed end and an opposite end, whereby the opposite end of the lancet is disposed in communication with the substrate and located at the reaction area.

An aspect of an embodiment of the present invention provides, among other things, a system for determining the amount of an analyte in a liquid sample received from a subject. The system may comprise an analyte meter (or a portion of an analyte meter; or other type of meter as suitable) configured to receive data from an electrochemical biosensor test strip device. Next, the test strip device (or a portion of the test strip device) may comprise: a substrate having a liquid sampling end and an electrical contact end; a circuit disposed in communication with the substrate, wherein the circuit having a meter engagement end configured to engage and communicate with the analyte meter; a reaction area formed at the liquid sampling end of the substrate; and a lancet having a pointed end and an opposite end, whereby the opposite end of the lancet is disposed in communication with the substrate and located at the reaction area.

An aspect of an embodiment of the present invention provides, among other things, a method of making an electrochemical biosensor test strip device for determining the amount of an analyte in a liquid sample received from a subject. The method may comprise: providing a substrate having a liquid sampling end and an electrical contact end; applying a circuit disposed in communication with the substrate; applying a reaction area formed at the liquid sampling end of the substrate; and mounting, attaching, or communicating a lancet having a pointed end and an opposite end, whereby the opposite end of the lancet is disposed in communication with the substrate and located at the reaction area. The method may further comprise making or providing a meter or portions of a meter compatible for use with the strip device.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS

An aspect of an embodiment of the present invention provides, among other things, an electrochemical biosensor test strip device (and related method) for determining the amount of analyte in a liquid sample received from a subject. For the purpose of this disclosure, the determination of the analyte may include one or more of the following: detecting, measuring or analyzing the analyte, or determining a concentration of the analyte.

Figure 1:
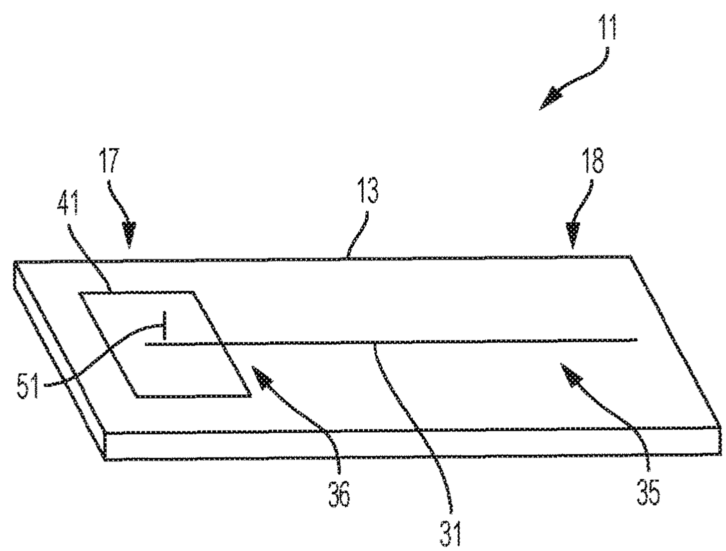
FIG. 1 schematically represents an aspect of an embodiment of an electrochemical biosensor test strip device.

FIG. 1 schematically represents an aspect of an embodiment of an electrochemical biosensor test strip device. In an embodiment, an electrochemical biosensor test strip device 11 is provided for determining the amount of an analyte in a liquid sample (not shown) received from a subject (not shown). As stated above, the determining the amount of the analyte may include one or more of the following: a) detecting the analyte, b) measuring the analyte, c) analyzing the analyte, or d) obtaining the concentration of the analyte. The device 11 may include: a substrate 13 having a liquid sampling end 17 and an electrical contact end 18; a circuit 31 disposed in communication with the substrate 13 having a meter engagement end 35 and reaction area engagement end 36; a reaction area 41 formed at the liquid sampling end 17 of the substrate 13; and a lancet 51 having a pointed end and an opposite end, whereby the opposite end of the lancet is disposed in communication with the substrate 13 and located at the reaction area 41. The lancet 51 may be configured to be stationary with the substrate 13.

Figure 2:
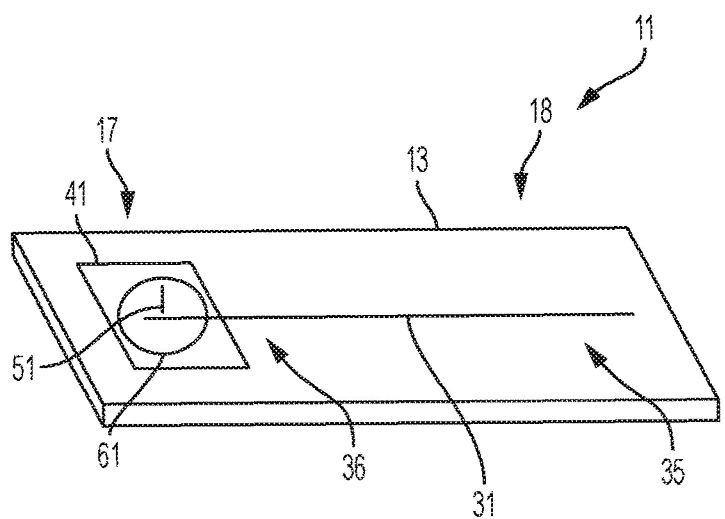
FIG. 2 schematically represents an aspect of an embodiment of an electrochemical biosensor test strip device of FIG. 1 that further includes an interface area.

FIG. 2 schematically represents an aspect of an embodiment of an electrochemical biosensor test strip device as depicted in FIG. 1 and which further includes an interface area 61 located at the liquid sampling end 17 of the substrate 13.

Figure 3A:
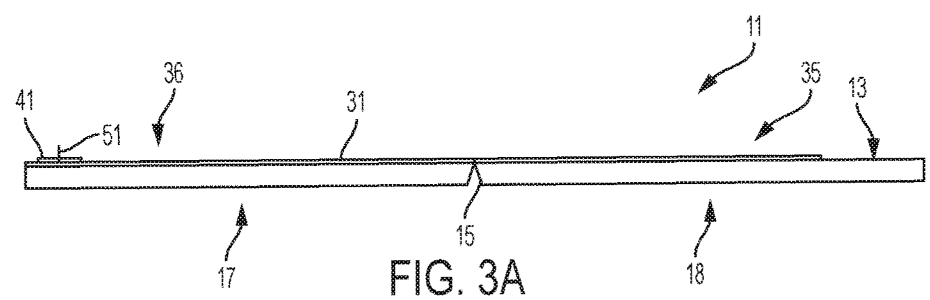
FIGS. 3A-3C schematically represents an aspect of an aspect of an embodiment of an electrochemical biosensor test strip device captured in the sequential positions of open, semi-open, and covered (or reversed or closed), respectively.
Figure 3B:
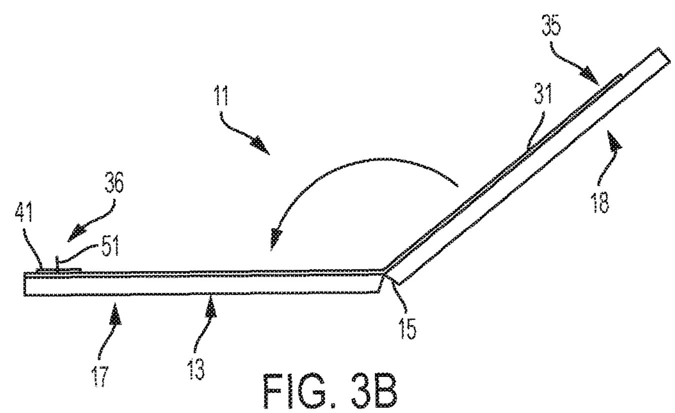
Figure 3C:
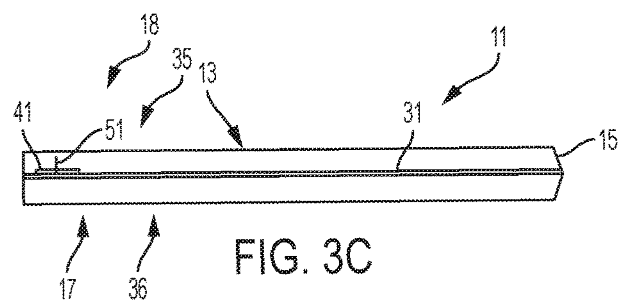

FIGS. 3A-3C schematically represents an aspect of an aspect of an embodiment of an electrochemical biosensor test strip device captured in the sequential positions of open, semi-open, and covered (or reversed or closed), respectively. In an embodiment, an electrochemical biosensor test strip device 11 is provided for determining the amount of an analyte in a liquid sample (not shown) received from a subject (not shown). The device 11 may include: a substrate 13 having a liquid sampling end 17 and an electrical contact end 18; a circuit 31 disposed in communication with the substrate 13 having a meter engagement end 35 and reaction area engagement end 36; a reaction area 41 formed at the liquid sampling end 17 of the substrate 13; and a lancet 51 having a pointed end and an opposite end, whereby the opposite end of the lancet is disposed in communication with the substrate 13 and located at the reaction area 41. The lancet 51 may be configured to be stationary with the substrate 13. Also provided is a pivot area 15 configured to assist in the capability and ease of the advancing from an open position to semi-open position and covered position (i.e., reversed or closed). The pivot area 15 may have a variety of configurations such as combination of one or more of the following: indentation, hinge device, weakened structure, thinned out area (compared to the proximal areas of the substrate), flap, pivot device, or perforation structure. Any configuration that augments or assists the substrate to bend or fold may be implemented as the pivot area 15. Although not illustrated, an interface area may be located at the liquid sampling end 17 of the substrate 13.

In an embodiment, the device 11 includes a substrate 13 configured whereby the electrical contact end 18 of the substrate 13 can be a) in an at least one open position relative to the liquid sampling end 17 of the substrate 13 and b) in at least one reversed position relative to the liquid sampling end of 17 of the substrate 13, whereby in the at least one reversed position causes the electrical contact end 18 of substrate 13 to be placed over top of the liquid sampling end 18. In an embodiment, the device 13 includes a pivot area 15 whereby the electrical contact end 18 of the substrate 13 pivots (relative to the liquid sampling end 17 of the substrate 18 at the pivot area 15 from the at least one open position to the at least one reversed position.

In an embodiment the lancet may be stationary. In an embodiment the lancet may be movable or removable. In an embodiment the lancet may pivot or change between an upright position (e.g., vertical) to a flat (e.g. horizontal), or vice versa.

Figure 4A:
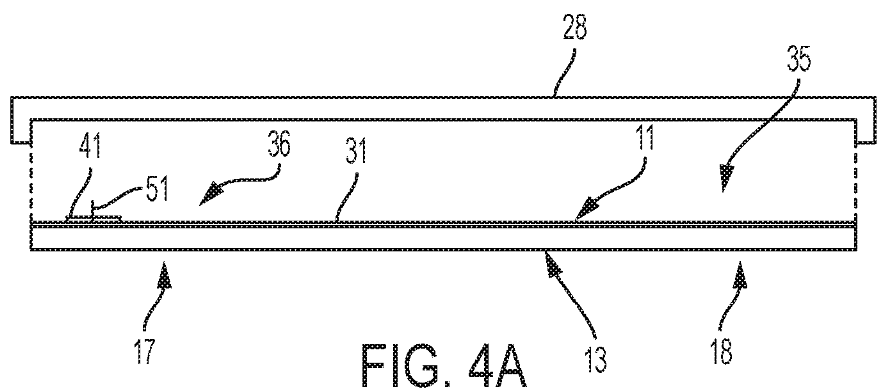
FIGS. 4A-4B schematically represents an aspect of an aspect of an embodiment of an electrochemical biosensor test strip device captured in the sequential positions of uncovered and covered, respectively.
Figure 4B:
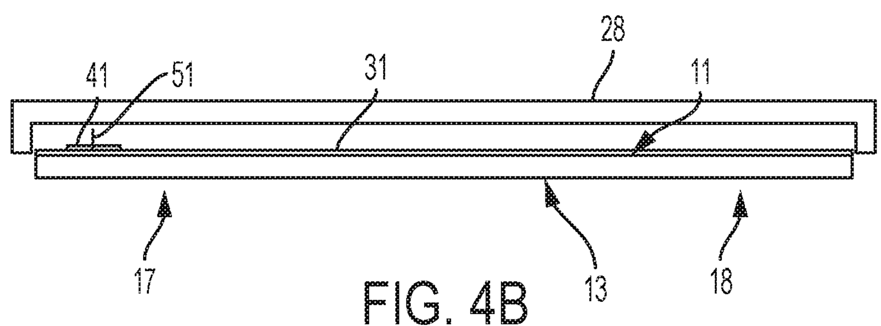

FIGS. 4A-4B schematically represents an aspect of an aspect of an embodiment of an electrochemical biosensor test strip device captured in the sequential positions of uncovered and covered, respectively. An electrochemical biosensor test strip device 11 is provided for determining the amount of an analyte in a liquid sample (not shown) received from a subject (not shown). The device 11 may include: a substrate 13 having a liquid sampling end 17 and an electrical contact end 18; a circuit 31 disposed in communication with the substrate 13 having a meter engagement end 35 and reaction area engagement end 36; a reaction area 41 formed at the liquid sampling end 17 of the substrate 13; and a lancet 51 having a pointed end and an opposite end, whereby the opposite end of the lancet is disposed in communication with the substrate 13 and located at the reaction area 41. The lancet 51 may be configured to be stationary with the substrate 13. In an embodiment the lancet may be movable, attachable, and/or removable. The device further includes a cover 28. The cover 28 may be a soft cover or hard cover. A cover 28 may have the rigidity that is equal to or less than or greater than the rigidity of the substrate 13. A cover 28 may be disposed on the device before use. A cover may be placed on the device after use. Different covers may be used before and after use. The cover may be a foil, film or wrap material suitable to cover the device before use (and/or after use). It's possible that a foil, film or wrap may be configured to be used to cover the device after use. A cover may be configured to set over the lancet 51. A cover may be removable from and/or attachable to the lancet 51. A cover may be configured to set over the lancet 51 and at least a portion of the substrate 13. A cover may be removable from and/or attachable to the lancet and at least a portion of the substrate, as well as any components of the device as well as the meter.

Figure 5:
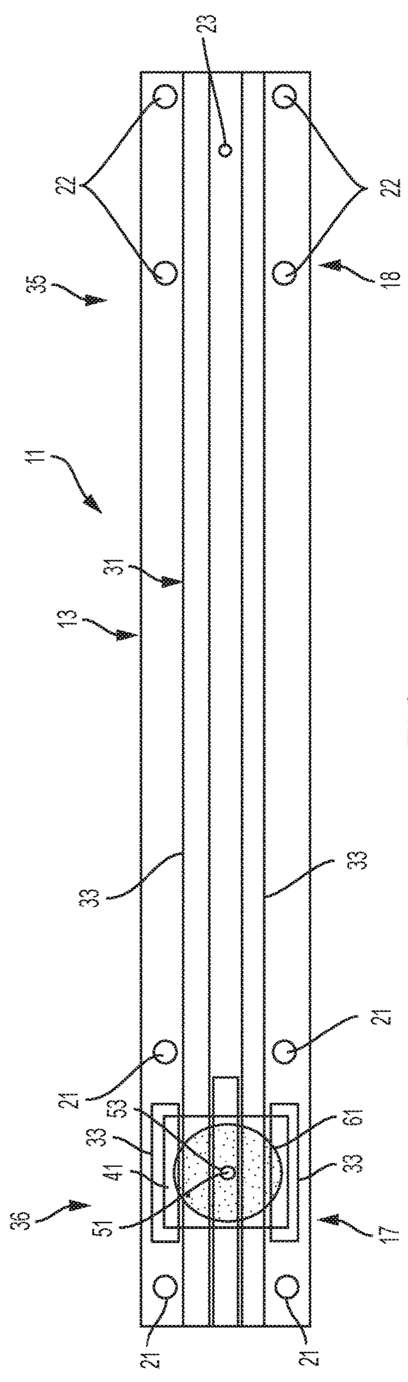
FIG. 5 schematically represents a plan view of an aspect of an embodiment of an electrochemical biosensor test strip device.

FIG. 5 schematically represents a plan view of an aspect of an embodiment of an electrochemical biosensor test strip device. In an embodiment, an electrochemical biosensor test strip device 11 is provided for determining the amount of an analyte in a liquid sample (not shown) received from a subject (not shown in FIG. 5). The device 11 may include: a substrate 13 having a liquid sampling end 17 and an electrical contact end 18; a circuit 31 comprised of conductors 33 disposed in communication with the substrate 13 having a meter engagement end 35 and reaction area engagement end 36; a reaction area 41 formed at the liquid sampling end 17 of the substrate 13; a lancet 51 having a pointed end and an opposite end, whereby the opposite end of the lancet is disposed in communication with the substrate 13 and located at the reaction area 41; and an interface area 61 located at the liquid sampling end 17 of the substrate 13. The lancet 51 may be configured to be stationary with the substrate 13. In an embodiment, the strip device 11 may be provided with a lancet channel 53 (or pathway, space, or conduit or the like) to accommodate the lancet 51 traversing from the substrate 13, reaction area 41, and/or circuit 31 from where it is stationed, connected, or secured thereto or other area from which it is stationed, connected, or secured. In an embodiment, the lancet 51 may traverse through the material or structure of the reaction area 41 itself without the use or implementation of a lancet channel 53 to accommodate the lancet.

Figure 6:
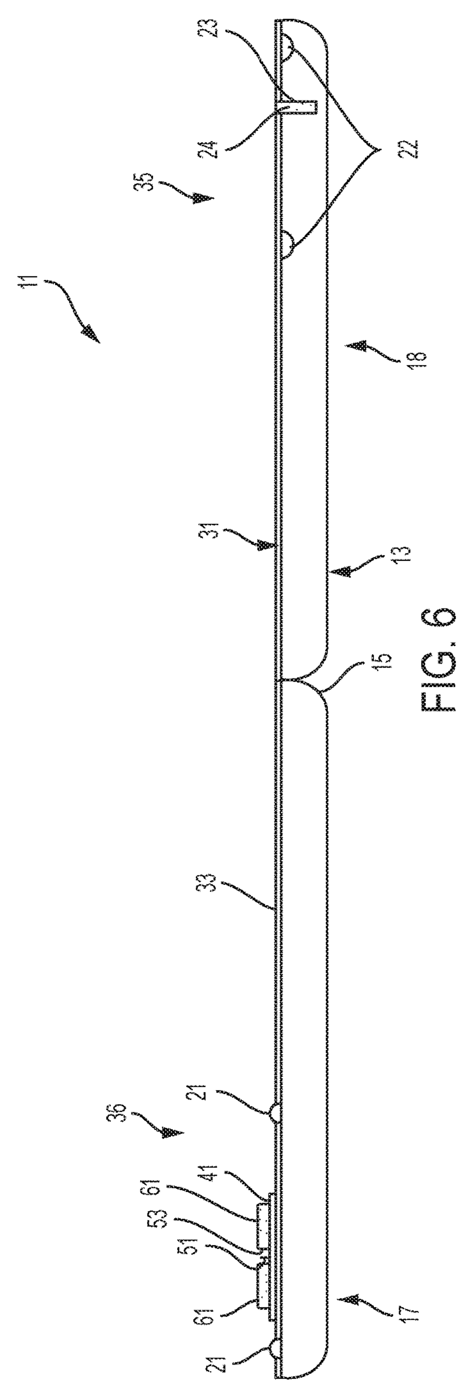
FIG. 6 schematically represents a side view of an aspect of an embodiment of an electrochemical biosensor test strip device, as shown in FIG. 5.

FIG. 6 schematically represents a side view of an aspect of an embodiment of an electrochemical biosensor test strip device as shown in FIG. 5. In an embodiment, the electrical contact end 18 of the substrate 13 may have a sleeve recess 23 (e.g., channel, hollow space, tunnel or the like) to accommodate the lancet 51 when the electrical contact end 18 of the substrate 13 is folded over or placed on top of the liquid sampling end 17 of the substrate 13 (for example, see FIG. 10). In an embodiment, the sleeve recess 23 may have an absorbent material or structure 24 to absorb or contain the withdrawn liquid sample as the sleeve recess 23 is folded over or placed on top of the lancet 51 (for example see FIG. 10).

Figure 7:
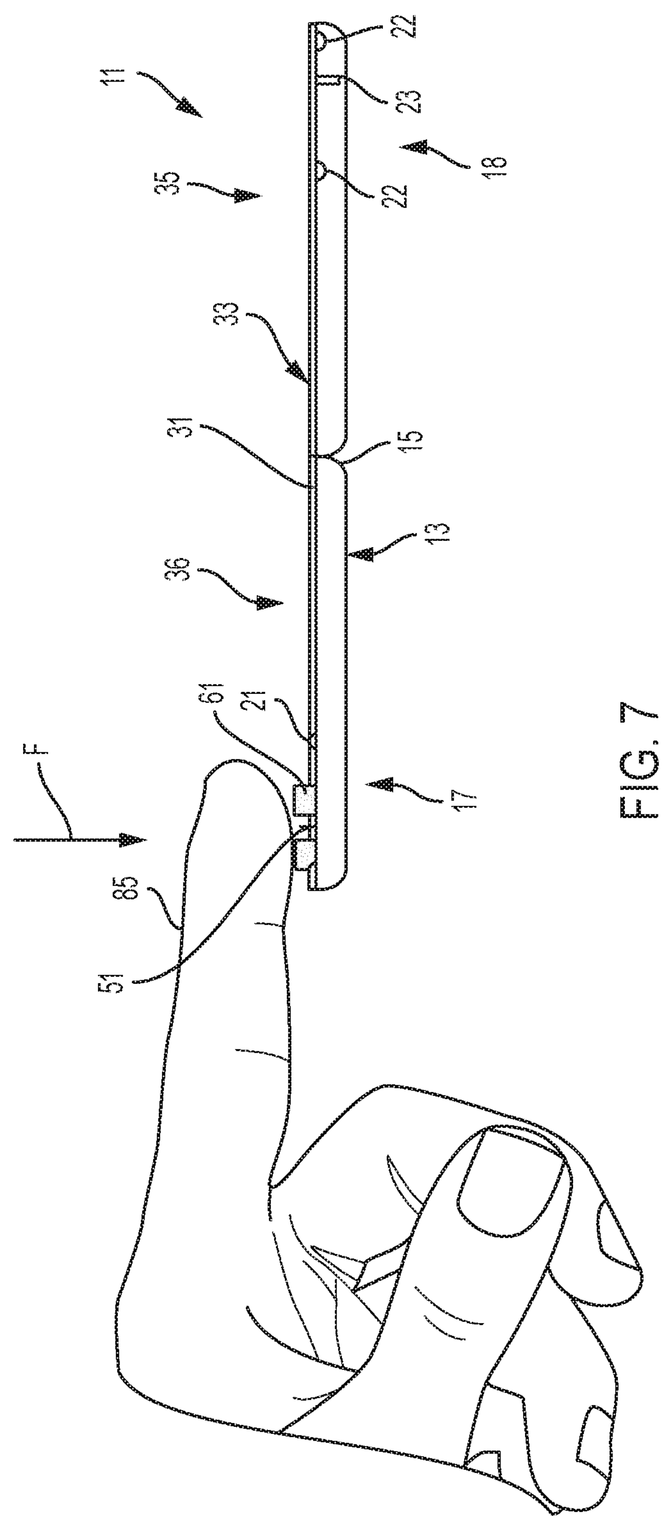
FIG. 7 schematically represents a side view of an aspect of an embodiment of an electrochemical biosensor test strip device whereby a subject is engaging therewith.

FIG. 7 schematically represents a side view of an aspect of an embodiment (as shown in FIGS. 5 and 6) of an electrochemical biosensor test strip device whereby a subject 85 is engaging therewith at the reaction area 41. As shown, the subject is about to apply a force F to the device so to pierce the subject's skin with the lancet 51 to draw a liquid sample (e.g., blood). Aspects of the device 11 is configured whereby drawn liquid sample (e.g., blood) will travel to the reaction area (not shown in FIG. 7). In an embodiment (not shown), a spring-like force or drive-like force mechanism, structure, or material may be included originating generally opposite the reaction area 41 on the opposite side of the substrate (or at or in communication with the substrate) so as to provide a force on the device (lancet) to drive it into the subject (such force exerted by the device (lancet) would be generally be directed opposite to the force F as illustrated). As such, the portion of the device (or lancet) drives the lancet upward, rather than the subject having to apply the force into the lancet (i.e., downward into the lancet).

In an embodiment, the reaction area 41 may be a reagent film that is formed by drying a mixture of reagents containing at least one biological active substance (e.g., enzyme) and other components such as mediator, surfactant, and at least one binder. Enzymes suitable for use are ones that are responsible for the chemical reaction of the analyte. Examples of a preferred enzyme are glucose oxidase or glucose dehydrogenase for measuring the analyte glucose. For measuring the analyte uric acid, the enzyme is preferably uricase. For measuring the analyte cholesterol, the enzymes are preferably cholesterol oxidase and cholesterol esterase. Other enzymes may be implemented other than the ones specifically listed herein. Suitable mediator for use is the material which is capable of undergoing reversible, oxidation-reduction reaction and electron transferring. Eight common analytes used in laboratory assays include, but not limited thereto, creatinine, glucose, phosphate, uric acid, total cholesterol, HDL cholesterol, LDL cholesterol, and triglycerides. A variety of available analytes may be applied using the various embodiments (or aspects thereof) of the systems and methods of the present invention. A variety of meters and types of meters may be implemented as compatible with the analytes listed above or any other analytes or materials. Similarly, a variety of meters and types of meters may be implemented as compatible with a variety of circuits, conductors, or electronics as desired or required and for a variety of diagnostics and assays as desired and required.

In an embodiment pertaining to measuring the analyte glucose, the chemical mixture of the reaction area 41 assists in turning glucose into electricity that include, for example, the enzyme and the mediator, among other ingredients. The enzyme is a protein that latches onto glucose in the blood sample and removes a couple of the sugar's electrons. The enzyme passes these electrons to a mediator, a molecule quickly passes the electrons off to the circuit 33. Next, electrons from glucose travel through the conductors (e.g., network of wires) from the reaction area to the meter 71 (e.g., glucose meter). The meter counts the electrons as current and calculates how much glucose it took to generate that much electricity. The meter displays that number on its screen and/or communicates it remotely.

In an embodiment, the device may be utilized to monitor the effects of warfarin, which is called the International Normalized Ratio (INR). For example, the INR is a blood test that checks how long it takes for blood to clot. The higher the INR, the longer it will take blood to clot (and the higher the risk of bleeding). The device may be applied to analyze the warfarin and INR as desired or required. In an embodiment, the device may be utilized for point-of-care (POC) cholesterol screenings.

In an embodiment the reaction area may comprises one or more enzymes selected to facilitate a reaction with the analyte. In an embodiment the analyte may comprise glucose, wherein the one or more enzymes may comprise glucose oxidase or glucose dhydrogenase or both glucose oxidase and glucose dhydrogenase. In an embodiment the analyte may comprise uric acid, wherein the one or more enzymes may comprise uricase. In an embodiment the analyte may comprise cholesterol, wherein the one or more enzymes may comprise cholesterol oxidase or cholesterol esterase or both cholesterol oxidase and cholesterol esterase.

Figure 8:
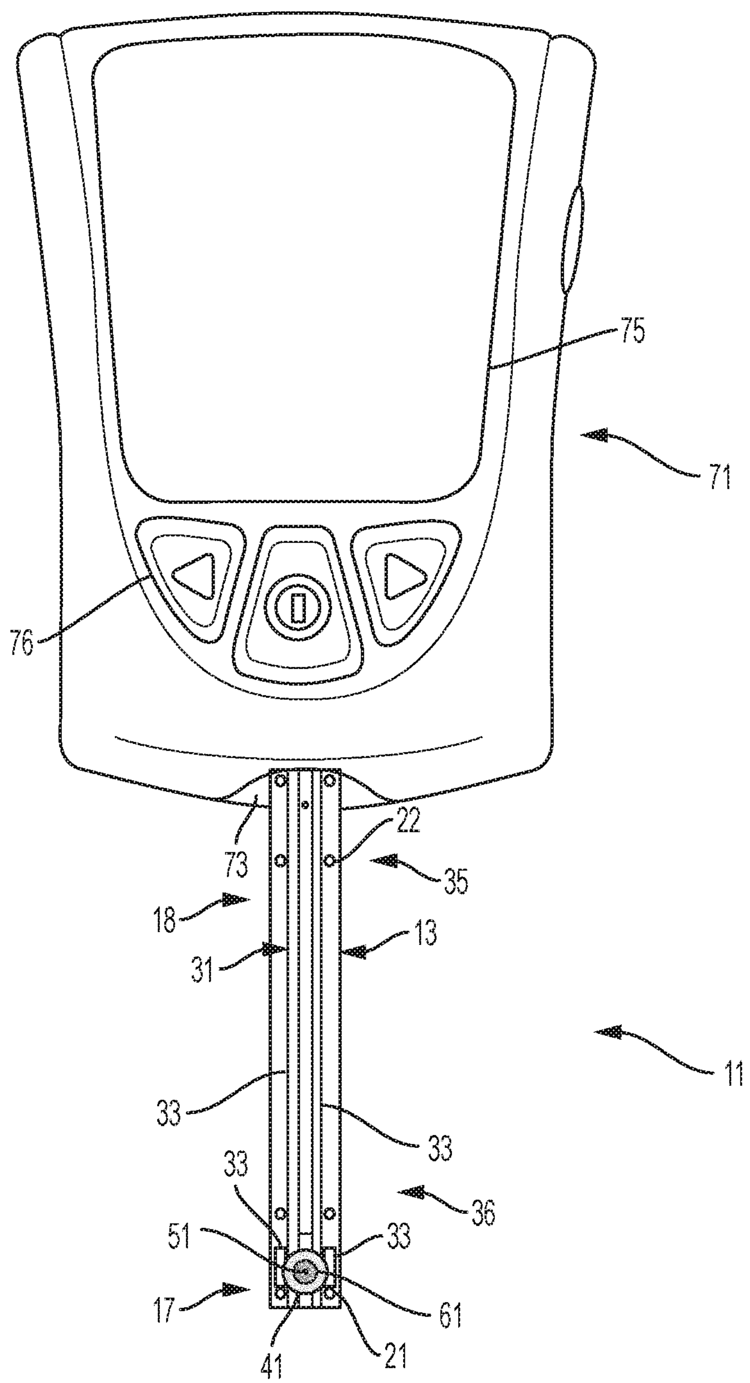
FIG. 8 schematically represents a plan view of an aspect of an embodiment of an electrochemical biosensor test strip device in communication with a meter.

FIG. 8 schematically represents a plan view of an aspect of an embodiment of an electrochemical biosensor test strip device 11 in communication with a meter 71. In an embodiment, circuit 31 includes a meter engagement end 35 configured to engage and communicate with an analyte meter 71 at the conductor engagement area 73 (or via other appropriate interface or connection) of the meter 71. In an embodiment, the substrate 13 includes an electrical contact end 18 configured to engage and communicate with an analyte meter 71 at the conductor engagement area 73 (or via other appropriate interface or connection) of the meter 71. In an embodiment, the circuit 31 may comprise a reaction area engagement end 36 configured to receive electrical signals provided by the reaction area 41. In an embodiment, the reaction area 41 may comprise one or more enzymes selected to facilitate a reaction with the analyte (of the liquid sample) to provide electrical signals. In an embodiment, the circuit 31 may comprise a meter engagement end 35 configured to provide, communicate, exchange or transmit the electrical signals with the meter 71 and/or other processor-based device (system) or electronic device (system).

Figure 9:
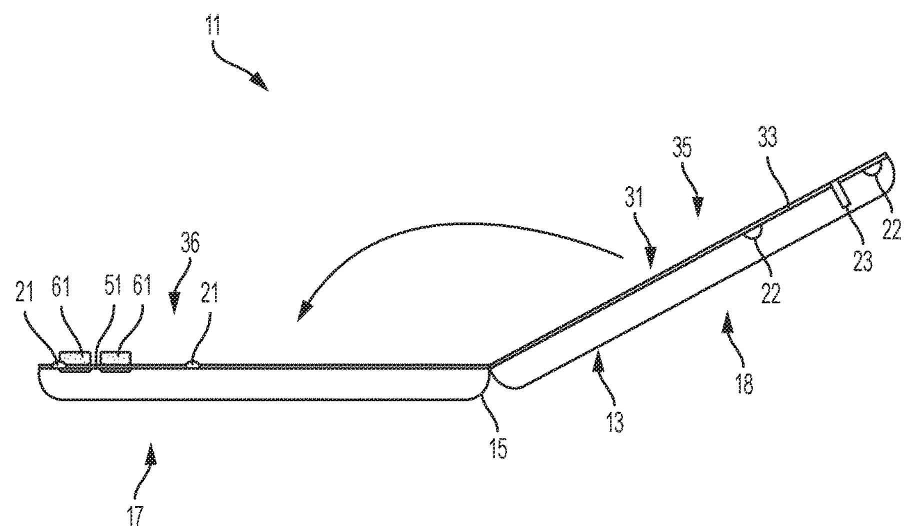
FIGS. 9-10 schematically represents an aspect of an aspect of an embodiment of an electrochemical biosensor test strip device captured in the sequential positions of semi-open and covered (or reversed or closed), respectively.
Figure 10:
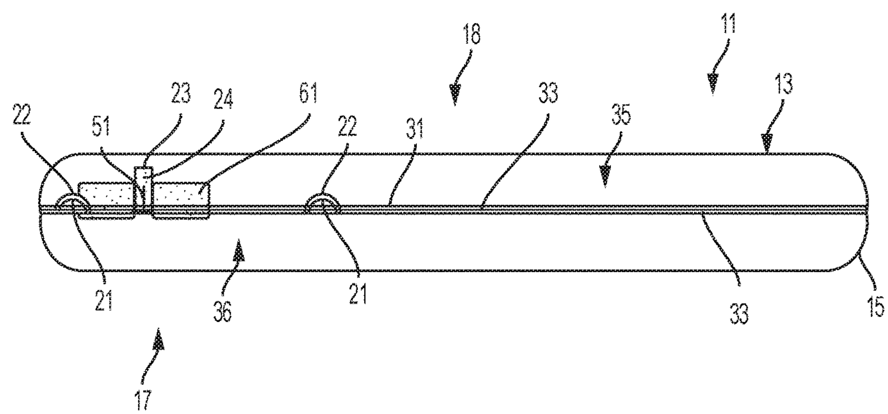

FIGS. 9-10 schematically represents an aspect of an aspect of an embodiment (as shown in FIGS. 5 and 6) of an electrochemical biosensor test strip device 11 captured in the sequential positions of semi-open and covered (or reversed or closed), respectively. In an embodiment, the biosensor test strip device 11 may include any sort of fastening, attaching or securing means, devices, structures or materials. For example, a Velcro arrangement disposed on the opposing portions of the biosensor test strip device 11 so that when the biosensor test strip device 11 is in a covered position (e.g., reversed or closed) the respective Velcro means attach to one another. For example, in an embodiment, a latch fastener device or catch may be provided on opposing portions of the biosensor test strip device 11 so as to accomplish the fastening or securing. For example, in an embodiment, an adhesive material may disposed on one or more opposing portions so as to accomplish the fastening or securing. For example, in an embodiment, a clasp fastener device or mechanism may be provided on opposing portions of the biosensor test strip device 11. For instance, in a particular approach, as shown in some of the illustrations herein (e.g., FIGS. 5-10) respective clasp recesses 22 and clasp protrusions or bumps 21 may be provided on opposing portions of the biosensor test strip device 11 that mate with one another to assist in catching, locking, securing, or stabilizing the opposing portions of the device in the covered position (e.g., reversed or closed).

Figure 11A:
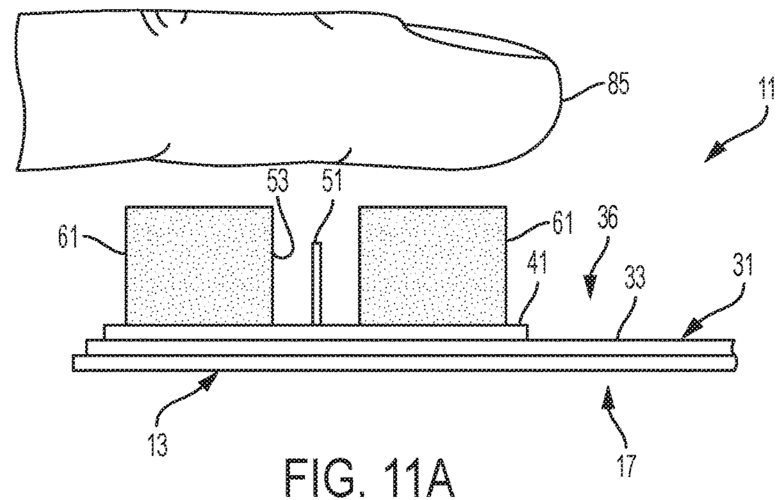
FIGS. 11A-11B schematically represents a partial side view of an aspect of an embodiment of an electrochemical biosensor test strip device whereby a subject is engaging therewith whereby the interface area is in a rest (non-contact) position and compressed (engaged) position, respectively.
Figure 11B:
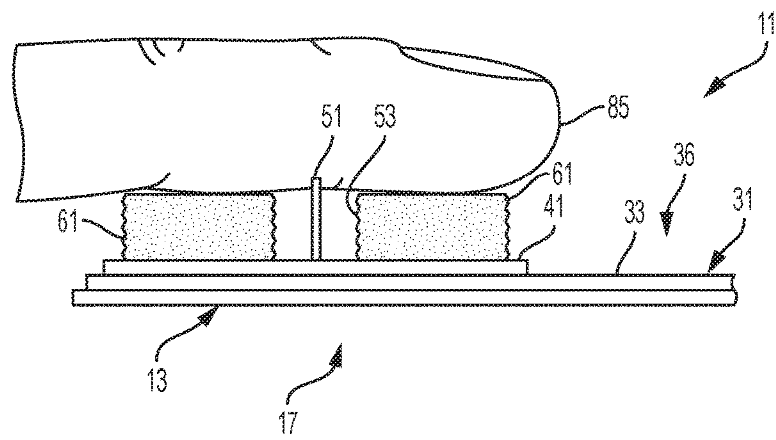

FIGS. 11A-11B schematically represents a partial side view of an aspect of an embodiment of an electrochemical biosensor test strip device 11 whereby a subject 85 is engaging therewith whereby the interface area 61 is in a rest (non-contact) position or state and compressed (engaged) position or state, respectively. In an approach, the subject 85 will engage the interface area 61 and apply a Force F. The Force F applied by the subject 85 will compress or deform the interface area 61 from a rest position or state (FIG. 11A) to a deformed (compressed or reduced) position or state (FIG. 11B) to allow the lancet 51 to pierce the skin of the subject 85 to drawn the liquid sample (blood). Accordingly, in an embodiment, the interface area 61 is configured to be deformable from a rest position to a deformed position (or reduced topography height) upon receiving force exerted by the subject. The interface area is configured to have a vertical height in the rest position that extends above the pointed end of the lancet. The interface area is configured to have a vertical height in the deformed position that extends below the pointed end of the lancet so as to allow the subject to be pierced by the lancet. The drawn liquid sample (not shown s collected on the reaction area 41, and the meter 71 (not shown in FIG. 11) can then analyze or process the liquid sample for determining the amount of analyte (e.g., analyte concentration or measurement, etc.).

In an alternative embodiment, the interface area is configured to have a vertical height that is below the pointed end of the lancet so as to allow the subject to be pierced by the lancet. In such an alternative embodiment, the lancet is taller than the height of the interface area, thus eliminating the need for deforming or reducing the height of the interface area.

In an embodiment, the reaction area may be integrated as part of the interface area. As such, the reaction area would be multifunctional as it would not only perform its reaction function as disclosed herein, but it would also act and serve as an interface area as discussed (i.e., provide the interface area function).

Alternatively, both the reaction area component may remain as well as the reaction area component, but the reaction area function could also be added into the interface area. Thus, the interface area could also perform the reaction area functions.

Figure 12:
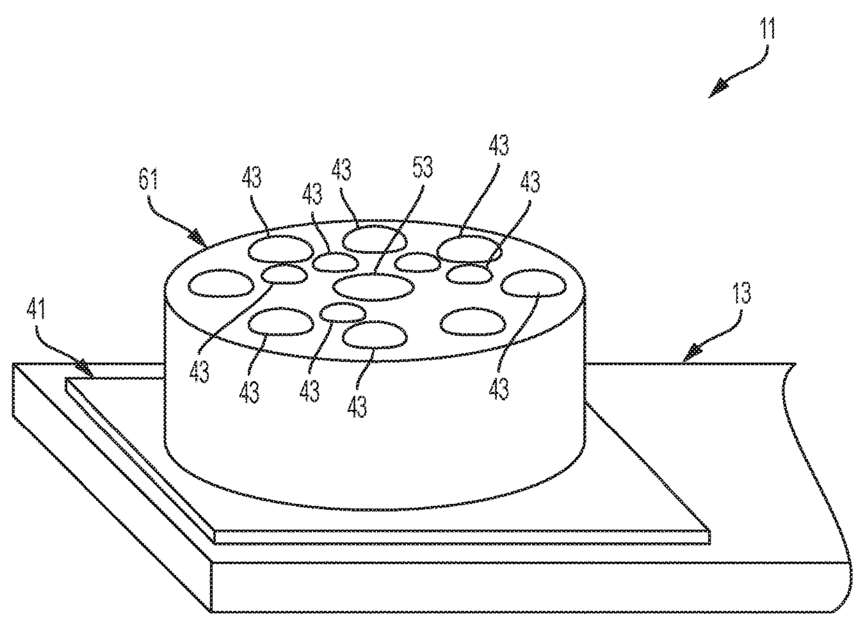
FIG. 12 schematically represents a partial perspective view of an aspect of an embodiment of an electrochemical biosensor test strip device generally capturing the substrate, interface area and sensory points.

FIG. 12 schematically represents a partial perspective view of an aspect of an embodiment of an electrochemical biosensor test strip device 11 generally capturing the substrate 13, interface area 61, and sensory points 43 (e.g., raised bed of protrusions or bumps). In an embodiment, the interface area 61 comprises a plurality of blunt contact points 43 disposed on its surface that provides sensory signal distraction to the subject during physical contact by the subject. The sensory contact points 43 may be configured, for example but not limited thereto, as protrusions or bumps. They may be a variety of sizes and spaced with a variety of patterns (uniform or non-uniform/stochastic) across the surface of the interface.

Figure 13:
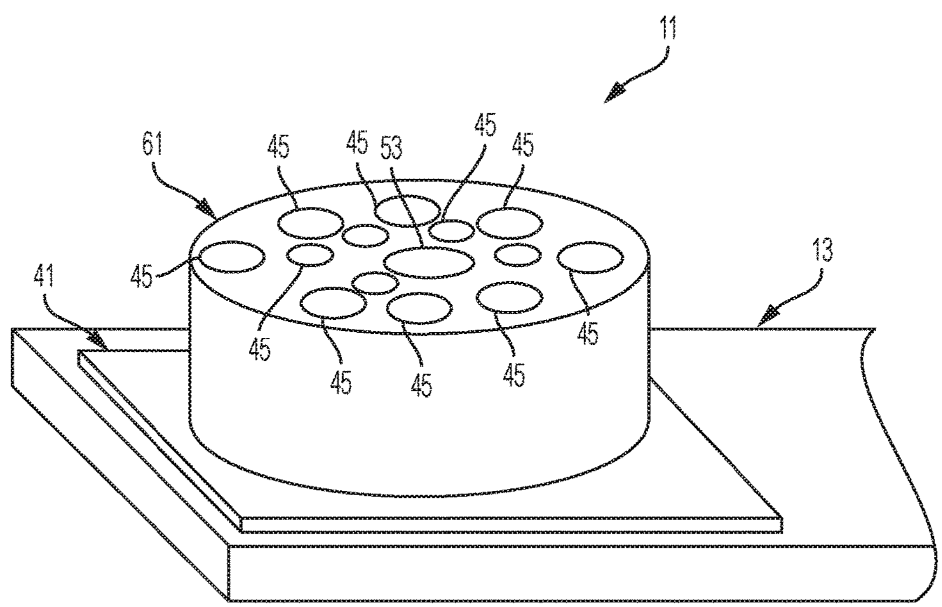
FIG. 13 schematically represents a partial perspective view of an aspect of an embodiment of an electrochemical biosensor test strip device generally capturing the substrate, interface area and pores or capillaries.

FIG. 13 schematically represents a partial perspective view of an aspect of an embodiment of an electrochemical biosensor test strip device 11 generally capturing the substrate 13, interface area 61, and pores or capillaries 45. In an embodiment, the interface area 61 may be a variety of materials and structures to provide an absorptive function to aid in the liquid sample obtained from the subject to travel to the reaction area 41 (not shown in instant Figure). For example, the interface area 61 may be a comprised of a plurality of pores 45 or capillaries 45. For example, the capillaries 45 may be configured to provide a capillary force to carry the drawn liquid sample from the subject to the reaction area. The pores 45 may configured as channels, channels, vias, or conduits to carry the drawn liquid sample from the subject. They may be a variety of sizes and spaced with a variety of patterns (uniform or non-uniform/stochastic) across the surface of the interface.

In an embodiment, the device may be operable without a raised interface area, or the structure of the interface area may be omitted altogether, due to the fact that the lancet 51 is disposed within and at the reaction area 41 thereby assuring that the withdrawn liquid sample from the subject is deposited directly to the reaction area at the time that the skin is being pierced.

In an embodiment, rather than pivoting or bending, the device may be configured wherein the electrical contact end 18 of the substrate 13 and the liquid sampling end 17 of the substrate 13 are configured to be separable relative to each other. Separation may be provided by, but not limited thereto, modular connectivity, perforations, weakened material/structure, thinning of material or structure, or cutting or tearing, or other possible and suitable techniques. Further, wherein the separated electrical contact end 18 is configured to be positioned and cover the separated liquid sampling end 17 so as to cover the lancet 51.

It should be appreciated that various sizes, dimensions, contours, rigidity, shapes, flexibility and materials of any of the components or portions of components in the various embodiments discussed throughout may be varied and utilized as desired or required. The lancet gauge size, contour, material, and length may vary as desired or required. The size, design, contour, material, and type of electronic components, circuitry, and hardware of the strip device may vary as desired or required. The size, dimensions, contour, and material(s) of the substrate may vary as desired or required. The meter type, meter size, contour, of meter, meter-interface, meter-display, meter local and remote communications, meter electronics, and meter model type may vary as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

It should be appreciated that the strip device and related components discussed herein may can take on all shapes along the entire continual geometric spectrum of manipulation of x, y and z planes to provide and meet the anatomical and structural demands, operational and requirements.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example. It should be appreciated that the device may be applied or directed to any region or target on the subject. It should be appreciated that the device may have a variety of contours, shapes, and sizes to be compatible for being applied or directed to any region or target on the subject. It should be appreciated that the device may be integral with or connected (electronic communication and/or physical communication) to any accessories or medical devices worn or used by the subject.

EXAMPLES

Practice of an aspect of an embodiment (or embodiments) of the invention will be still more fully understood from the following examples and experimental results, which are presented herein for illustration only and should not be construed as limiting the invention in any way.

Example 1

An electrochemical biosensor test strip device for determining the amount of an analyte in a liquid sample received from a subject. The device may comprise: a substrate having a liquid sampling end and an electrical contact end; a circuit disposed in communication with the substrate; a reaction area formed at the liquid sampling end of the substrate; and a lancet having a pointed end and an opposite end, whereby the opposite end of the lancet is disposed in communication with the substrate and located at the reaction area.

Example 2

The device of example 1, wherein the communication of the lancet with the substrate is stationary relative to the substrate.

Example 3

The device of example 1 (as well as subject matter in whole or in part of example 2, in whole or in part), wherein the determining the amount of the analyte includes one or more of the following: detecting the analyte, measuring the analyte, analyzing the analyte, or obtaining the concentration of the analyte.

Example 4

The device of example 1 (as well as subject matter of one or more of any combination of examples 2-3, in whole or in part), further comprising an interface area located at the liquid sampling end of the substrate.

Example 5

The device of example 4 (as well as subject matter of one or more of any combination of examples 2-3, in whole or in part), wherein the interface area is configured to be deformable from a rest position to a deformed position upon receiving force exerted by the subject.

Example 6

The device of example 5 (as well as subject matter of one or more of any combination of examples 2-4, in whole or in part), wherein the interface area is configured to have a vertical height in the rest position that extends above the pointed end of the lancet.

Example 7

The device of example 6 (as well as subject matter of one or more of any combination of examples 2-5, in whole or in part), wherein the interface area is configured to have a vertical height in the deformed position that extends below the pointed end of the lancet.

Example 8

The device of example 4 (as well as subject matter of one or more of any combination of examples 2-3, in whole or in part), wherein the interface area comprises a plurality of blunt contact points disposed on its surface that provides sensory signal distraction to the subject during physical contact by the subject.

Example 9

The device of example 4 (as well as subject matter of one or more of any combination of examples 2-3 and 5-8), wherein the interface area is an absorptive material or structure.

Example 10

The device of example 4 (as well as subject matter of one or more of any combination of examples 2-3 and 5-9, in whole or in part), wherein the interface area is a porous material or structure.

Example 11

The device of example 4 (as well as subject matter of one or more of any combination of examples 2-3 and 5-10, in whole or in part), wherein the interface area is configured to provide a capillary force to carry the liquid sample from the subject to the reaction area.

Example 12

The device of example 1 (as well as subject matter of one or more of any combination of examples 2-11, in whole or in part), wherein the substrate is configured whereby the electrical contact end can be in an at least one open position relative to the liquid sampling end of the substrate and at least one reversed position relative to the liquid sampling end of the substrate, whereby in the at least one reversed position includes the electrical contact placed over top of the liquid sampling end.

Example 13

The device of example 12 (as well as subject matter of one or more of any combination of examples 2-11, in whole or in part), wherein the device includes a pivot area whereby the electrical contact end of the substrate pivots, relative to the liquid sampling end of the substrate, at the pivot area from the at least one open position to the at least one reversed position.

Example 14

The device of example 12 (as well as subject matter of one or more of any combination of examples 2-11 and 13, in whole or in part), further comprising a fastening material or fastening device disposed on the substrate for securing electrical contact end of the substrate to the liquid sampling end of the substrate in the reversed position.

Example 15

The device of example 1 (as well as subject matter of one or more of any combination of examples 2-14, in whole or in part), wherein the reaction area comprises one or more enzymes selected to facilitate a reaction with the analyte.

Example 16

The device of example 15 (as well as subject matter of one or more of any combination of examples 2-14, in whole or in part), wherein the analyte comprises glucose.

Example 17

The device of example 16 (as well as subject matter of one or more of any combination of examples 2-15, in whole or in part), wherein the one or more enzymes comprise glucose oxidase or glucose dhydrogenase or both glucose oxidase and glucose dhydrogenase.

Example 18

The device of example 15 (as well as subject matter of one or more of any combination of examples 2-14, in whole or in part), wherein the analyte comprises uric acid.

Example 19

The device of example 18 (as well as subject matter of one or more of any combination of examples 2-17, in whole or in part), wherein the one or more enzymes comprise uricase.

Example 20

The device of example 15 (as well as subject matter of one or more of any combination of examples 2-14, in whole or in part), wherein the analyte comprises cholesterol.

Example 21

The device of example 20 (as well as subject matter of one or more of any combination of examples 2-19, in whole or in part), wherein the one or more enzymes comprise cholesterol oxidase cholesterol esterase or both cholesterol oxidase and cholesterol esterase.

Example 22

The device of example 1 (as well as subject matter of one or more of any combination of examples 2-21, in whole or in part), wherein the circuit having a meter engagement end configured to engage and communicate with an analyte meter.

Example 23

The device of example 1 (as well as subject matter of one or more of any combination of examples 2-22, in whole or in part), wherein the circuit comprises a reaction area engagement end configured to receive electrical signals provided by the reaction area.

Example 24

The device of example 1 (as well as subject matter of one or more of any combination of examples 2-23, in whole or in part), wherein the reaction area comprises one or more enzymes selected to facilitate a reaction with the analyte to provide electrical signals.

Example 25

The device of example (as well as subject matter of one or more of any combination of examples 2-24, in whole or in part), wherein the circuit comprises a reaction area engagement end configured to receive the electrical signals.

Example 26

The device of example 1 (as well as subject matter of one or more of any combination of examples 2-25, in whole or in part), wherein the electrical contact end of the substrate and the liquid sampling end of the substrate are configured to be able to fold over or pivot relative to each other such that the electrical end of the substrate folds over the liquid sampling end of the substrate so as to cover the lancet.

Example 27

The device of example 26 (as well as subject matter of one or more of any combination of examples 2-25, in whole or in part), further comprising a channel disposed in the electrical contact end of the substrate configured to accommodate the lancet in the substrate fold over position.

Example 28

The device of example 1 (as well as subject matter of one or more of any combination of examples 2-27, in whole or in part, wherein the device further includes a cover configured to set over the lancet.

Example 29

The device of example 1, example 28 (as well as subject matter of one or more of any combination of examples 2-27 in whole or in part), wherein the cover is removable from and/or attachable to the lancet.

Example 30

The device of example 1 (as well as subject matter of one or more of any combination of examples 2-29 in whole or in part), wherein the device further includes a cover configured to set over the lancet and at least a portion of the substrate.

Example 31

The device of example 30 (as well as subject matter of one or more of any combination of examples 2-29 in whole or in part), wherein the cover is removable from and/or attachable to the lancet and at least a portion of the substrate.

Example 32

The device of example 31 (as well as subject matter of one or more of any combination of examples 2-30, in whole or in part, wherein the cover comprises a foil or wrap material.

Example 33

The device of example 1 (as well as subject matter of one or more of any combination of examples 2-32, in whole or in part), wherein the electrical contact end of the substrate and the liquid sampling end of the substrate are configured to be separable relative to each other.

Example 34

The device of example 33 (as well as subject matter of one or more of any combination of examples 2-32, in whole or in part), wherein separated electrical contact end is configured to be positioned and cover the separated liquid sampling end so as to cover the lancet.

Example 35

A system for determining the amount of an analyte in a liquid sample received from a subject. The system may comprise an analyte meter (or a portion of an analyte meter) configured to receive data from an electrochemical biosensor test strip device. Next, the test strip device (or a portion of the test strip device) may comprise: a substrate having a liquid sampling end and an electrical contact end; a circuit disposed in communication with the substrate, wherein the circuit having a meter engagement end configured to engage and communicate with the analyte meter; a reaction area formed at the liquid sampling end of the substrate; and a lancet having a pointed end and an opposite end, whereby the opposite end of the lancet is disposed in communication with the substrate and located at the reaction area.

Example 36

The system of example 35 (as well as subject matter of one or more of any combination of examples 1-34, in whole or in part), wherein the communication of the lancet with the substrate is stationary relative to the substrate.

Example 37

The system of example 35 (as well as subject matter of one or more of any combination of examples 1-34 and 36, in whole or in part), wherein the determining the amount of the analyte includes one or more of the following: detecting the analyte, measuring the analyte, analyzing the analyte, or obtaining the concentration of the analyte.

Example 38

The system of example 35 (as well as subject matter of one or more of any combination of examples 34 and 36-37, in whole or in part), further comprising an interface area located at the liquid sampling end of the substrate.

Example 39

A method of making an electrochemical biosensor test strip device for determining the amount of an analyte in a liquid sample received from a subject. The method may comprise: providing a substrate having a liquid sampling end and an electrical contact end; applying a circuit disposed in communication with the substrate; applying a reaction area formed at the liquid sampling end of the substrate; and mounting, attaching, or communicating a lancet having a pointed end and an opposite end, whereby the opposite end of the lancet is disposed in communication with the substrate and located at the reaction area. The method may further comprise making or providing a meter or portions of a meter compatible for use with the strip device.

Example 40

The method of example 39, further comprising: making a meter or portions of a meter compatible for use with said strip device. The method further comprises making any of the devices or systems or portions thereof) of any subject matter of one or more of any combination of examples 1-38, in whole or in part.

Example 41

The method of example 39, further comprising: providing a meter or portions of a meter compatible for use with said strip device. The method further comprises providing any of the devices or systems (or portions thereof) of any subject matter of one or more of any combination of examples 1-38, in whole or in part.

Example 42

The method of manufacturing any of the devices (structures or systems, or material) or their components or sub-components provided in any one or more of examples 1-38, in whole or in part.

Example 43

The method of using any of the devices structures or systems, or material) or their components or sub-components provided in any one or more of examples 1-38, in whole or in part.

Example 44

The method of providing instructions (or the computer readable medium of such instructions) of how to use any of the devices (structures or systems, or material) or their components or sub-components provided in any one or more of examples 1-38, in whole or in part.

REFERENCES

The devices systems, materials, compositions, reagents, substrates, components, sub-components, electronics, circuitry, meters, processors, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

1. International Patent Application Publication No. WO 02/100253 A2, Dbral, et al., "Blood Sampling Device with Diaphragm Actuated Lancet", Dec. 19, 2002.
2. U.S. Pat. No. 5,954,738, LeVaughn, et al., "Blood Sampling Device with Lancet Damping System", Sep. 21, 1999.
3. U.S. Pat. No. 7,175,643 B2, Shi, G., "Automatic Safe Self-Destructive Disposable Blood Sampling Device", Feb. 13, 2007.
4. U.S. Pat. No. 6,719,771 B1 Crossman, D., "Blood Sampling Device", Apr. 13, 2004.
5. U.S. Pat. No. 5,868,772, LeVaughn, "Blood Sampling Device with Anti-Twist Lancet Holder", Feb. 9, 1999.
6. U.S. Pat. No. 4,858,607, Jordan, et al., "Plastic Device for Injection and Obtaining Blood Samples", Aug. 22, 1989.
7. U.S. Patent Application Publication No. US 2003/0088191 A1, Freeman, et al., "Blood Sampling Device with Diaphragm Actuated Lancent", May 8, 2003,
8. U.S. Pat. No. 5,707,384, Kim, I., "Lancet Device for Obtaining Blood Samples", Jan. 13, 1998.
9. U.S. Pat. No. 7,972,349 B2, Crossman, et al., "Blood Sampling Devices", Jul. 5, 2011.
10. U.S. Patent Application Publication No. US 2009/0299224 A1, Yoo, J., "Dec. 3, 2009.
11. U.S. Patent Application Publication No. US 2006/0129172 A1, Crossman, et al., "Blood Sampling Device", Jun. 15, 2006.
12. U.S. Pat. No. 6,468,287 B1, Baugh, R., "Lancet for Capillary Puncture Blood Samples", Oct. 22, 2002.
13. U.S. Pat. No. 7,112,265 B1, McAleer, J., et al., "Disposable Test Strips with Integrated Reagent/Blood Separation Layer", Sep. 26, 2006.

14. U.S. Patent Application Publication No. US 2007/0193882 A1, Dai, K., et al., "Electrochemical Test Strip for Multi-Functional Biosensor", Aug. 23, 2007.
15. U.S. Pat. No. 7,875,461 B2, Docherty, E., et al., "Test Strip and Connector", Jan. 25, 2011.
16. U.S. Patent Application Publication No. US 2004/0006285 A1, Douglas, J., et al., "Methods and Apparatus for Sampling and Analyzing Body Fluid", Jan. 8, 2004.
17. U.S. Patent Application Publication No. US 2005/0240119 A1, Draudt, G., et al., "Blood Glucose Meter Having Integral Lancet Device and Test Strip Storage Vial for Single Handed Use and Methods for Using Same", Oct. 27, 2005.
18. U.S. Patent Application Publication No. US 2004/0182703 A1, Bell, D., et al., "Systems and Methods for Blood Glucose Sensing", Sep. 23, 2004.
19. U.S. Patent Application Publication No. US 2009/0302872 A1, Haggett, B., et al., "Electrochemical Strip for use with a Multi-Input Meter", Dec. 10, 2009.
20. U.S. Patent Application Publication No. US 2009/0057146 A1, Teodorczyk, M., et a "Analyte Test Strip with Improved Reagent Deposition", Mar. 5, 2009.
21. U.S. Patent Application Publication No. US 2011/0284393 A1, Macfie, G., et al., "Analytical Test Strip with an Electrode Having Electrochemically Active and Inert Areas of a Predetermined Size and Distribution", Nov. 24, 2011.
22. U.S. Patent Application Publication No. US 2008/0208078 A1, Neel, G., et al., "Test Strip with integrated Lancet", Aug. 28, 2008.
23. U.S. Patent Application Publication No. US 2010/0198107 A1, Groll, H., et al., "Integrated Blood Glucose Meter and Lancing Device", Aug. 5, 2010.
24. U.S. Patent Application Publication No. US 2010/0081968 A1, Neel, G., et al., "Test Strip with Integrated Lancet", Apr. 1, 2010.
25. U.S. Pat. No. 6,264,619 B1, Ferguson, M., "Kit for Drawing a Blood Sample", Jul. 24, 2001.
26. European Patent Application Publication No. EP 0874984 B1, Hill, B., et al., "Electrochemical Biosensor Test Strip", Nov. 18, 2001.
27. U.S. Pat. No. 7,378,007 B2, Moerman, P., et al., "Combined Lancet and Electrochemical Analyte-Testing Apparatus", May 27, 2008.
28. U.S. Pat. No. 8,636,672 B2, Neel, G., et al., "Test Strip with Integrated Lancet", Jan. 28, 2014.
29. U.S. Pat. No. 6,706,159 B2, Moerman, P., et al., "Combined Lancet and Electrochemical Analyte-Testing Apparatus", Mar. 16, 2004.
30. U.S. Patent Application Publication No. US 2006/0229532 A1, Wong, D., et al., "Integrated Lancing Test Strip with Retractable Lancet", Oct. 12, 2006.
31. U.S. Pat. No. 8,025,628 B2, Wong, D., et al, "Integrated Lancing Test Strip with Retractable Lancet", Sep. 27, 2011.
32. U.S. Pat. No. 7,374,546 B2, Roe, S., et al., "Integrated Lancing Test Strip", May 20, 2008.
33. U.S. Pat. No. 5,951,492, Douglas, J., et al., "Methods and Aparatus for Sampling and Analyzing Body Fluid", Sep. 14, 1999.
34. U.S. Pat. No. 7,343,188 B2, Sohrab, B., "Devices and Methods for Accessing and Analyzing Physiological Fluid", Mar. 11, 2008.
35. U.S. Pat. No. 6,099,484, Douglas, J., et al., "Methods and Apparatus for Sampling and Analyzing Body Fluid", Aug. 8, 2000.
36. U.S. Pat. No. 8,357,107 B2, Draudt, G., et al., "Blood Glucose Meter Having integral Lancet Device and Test Strip Storage Vial for Single Handed Use and Methods for Using Same", Jan. 22, 2013.
37. U.S. Patent Application Publication No. US 2008/0021291 A1, Zocchi, M., "Integrated Lancet and Blood Glucose Meter System", Jan. 24, 2008.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. An electrochemical biosensor test strip device for determining the amount of an analyte in a liquid sample received from a subject, wherein said device comprises:

a) a substrate having a liquid sampling end and an electrical contact end;

b) a circuit disposed in communication with said substrate;

c) a reaction area formed at said liquid sampling end of said substrate;

d) an interface area located at the liquid sampling end of said substrate;

e) a lancet having a pointed end and an opposite end, whereby said opposite end of said lancet is disposed on said substrate and located at said reaction area; and wherein said electrical contact end of said substrate and said liquid sampling end of said substrate are configured to be able to fold over or pivot relative to each other such that said electrical end of said substrate folds over said liquid sampling end of said substrate so as to cover said lancet.

2. The device of claim 1, wherein said lancet is stationary relative to said substrate.

3. The device of claim 1, wherein said determining the amount of the analyte includes one or more of the following:

detecting the analyte, measuring the analyte, analyzing the analyte, or obtaining the concentration of the analyte.

4. The device of claim 1, wherein said interface area is configured to be deformable from a rest position to a deformed position upon receiving force exerted by the subject.

5. The device of claim 4, wherein said interface area is configured to have a vertical height in the rest position that extends above the pointed end of said lancet.

6. The device of claim 5, wherein said interface area is configured to have a vertical height in the deformed position that extends below the pointed end of said lancet.

7. The device of claim 1, wherein said interface area comprises a plurality of blunt contact points disposed on its surface that provides sensory signal distraction to the subject during physical contact by the subject.

8. The device of claim 1, wherein said interface area is an absorptive material or structure.

9. The device of claim 1, wherein said interface area is a porous material or structure.

10. The device of claim 1, wherein said interface area is configured to provide a capillary force to carry the liquid sample from the subject to said reaction area.

11. The device of claim 1, wherein said device includes a pivot area whereby said electrical contact end of said substrate pivots, relative to said liquid sampling end of said substrate, at said pivot area from said at least one open position to said substrate fold over position.

12. The device of claim 1, further comprising a fastening material or fastening device disposed on said substrate for securing the electrical contact end of said substrate to said liquid sampling end of said substrate in said substrate fold over position.

13. The device of claim 1, wherein said reaction area comprises one or more enzymes selected to facilitate a reaction with the analyte.

14. The device of claim 13, wherein said analyte comprises glucose.

15. The device of claim 14, wherein the one or more enzymes comprise glucose oxidase or glucose dhydrogenase or both glucose oxidase and glucose dhydrogenase.

16. The device of claim 13, wherein said analyte comprises uric acid.

17. The device of claim 16, wherein the one or more enzymes comprise uricase.

18. The device of claim 13, wherein said analyte comprises cholesterol.

19. The device of claim 18, wherein the one or more enzymes comprise cholesterol oxidase or cholesterol esterase or both cholesterol oxidase and cholesterol esterase.

20. The device of claim 1, wherein said circuit has a meter engagement end configured to engage and communicate with an analyte meter.

21. The device of claim 1, wherein said circuit comprises a reaction area engagement end configured to receive electrical signals provided by said reaction area.

22. The device of claim 1, wherein said reaction area comprises one or more enzymes selected to facilitate a reaction with the analyte to provide electrical signals.

23. The device of claim 22, wherein said circuit comprises a reaction area engagement end configured to receive the electrical signals.

24. The device of claim 1, further comprising a channel disposed in said electrical contact end of said substrate configured to accommodate said lancet in said substrate fold over position.

25. An electrochemical biosensor test strip device for determining the amount of an analyte in a liquid sample received from a subject, wherein said device comprises:

a) a substrate having a liquid sampling end and an electrical contact end;

b) a circuit disposed in communication with said substrate;

c) a reaction area formed at said liquid sampling end of said substrate;

d) an interface area located at the liquid sampling end of said substrate;

e) a lancet having a pointed end and an opposite end, whereby said opposite end of said lancet is disposed on said substrate and located at said reaction area;

wherein said electrical contact end of said substrate and said liquid sampling end of said substrate are configured to be separable relative to each other;

wherein said electrical contact end can be in at least one open position and wherein said electrical contact position can be in at least one reverse position, and further wherein:

in said at least one open position said electrical contact end is in an one open position relative to said liquid sampling end of said substrate; and in said at least one reversed position said electrical contact end is placed on top of said liquid sampling end.

26. A system for determining the amount of an analyte in a liquid sample received from a subject, wherein said system comprises:

I) an electrochemical biosensor test strip device, said test strip device comprising:

a) a substrate having a liquid sampling end and an electrical contact end;

b) a circuit disposed in communication with said substrate, wherein said circuit has a meter engagement end configured to engage and communicate with an analyte meter;

c) a reaction area formed at said liquid sampling end of said substrate;

d) an interface area located at the liquid sampling end of said substrate;

e) a lancet having a pointed end and an opposite end, whereby said opposite end of said lancet is disposed on said substrate and located at said reaction area;

wherein said electrical contact end of said substrate and said liquid sampling end of said substrate are configured to be able to told over or pivot relative to each other such that said electrical end of said substrate folds over said liquid sampling end of said substrate so as to cover said lancet; and II) an analyte meter configured to receive data from said electrochemical biosensor test strip device.

27. The system of claim 26, wherein said lancet is stationary relative to said substrate.

28. The system of claim 26, wherein said determining the amount of the analyte includes one or more of the following:

detecting the analyte, measuring the analyte, analyzing the analyte, or obtaining the concentration of the analyte.

29. The device of claim 1, wherein said lancet is movable relative to said substrate, whereby said lancet can pivot or change between an upright position and a flat position relative to said substrate.

30. The device of claim 1, wherein said lancet is attachable to and/or removable from said substrate.

31. The device of claim 1, wherein said electrical contact end of said substrate and said liquid sampling end of said substrate are configured to be separable relative to each other.

32. The system of claim 26, further comprising a channel disposed in said electrical contact end of said substrate configured to accommodate said lancet in said substrate fold over position.

33. The device of claim 25, further comprising a channel disposed in said electrical contact end of said substrate configured to accommodate said lancet when said electrical contact is placed on top of said liquid sampling end.

34. The device of claim 25, wherein said circuit has a meter engagement end configured to engage and communicate with an analyte meter.

35. A kit comprising the device of claim 20 or claim 34, wherein the kit further comprises said analyte meter.

* * * * *